US012793849B2

(12) United States Patent
Soares et al.

(10) Patent No.: US 12,793,849 B2
(45) Date of Patent: Nov. 10, 2026

(54) INFORMATION PROCESSING SYSTEM, INFORMATION PROCESSING DEVICE, IMAGE ACQUISITION DEVICE, INFORMATION PROCESSING METHOD, IMAGE ACQUISITION METHOD, AND PROGRAM

(71) Applicants: NIKON CORPORATION, Tokyo (JP); Optos plc, Dunfermline (GB)

(72) Inventors: Devin Soares, Marlborough, MA (US); Branden Coleman, Marlborough, MA (US); Bradley Yates, Marlborough, MA (US); Koichi Odani, Tokyo (JP); Zhen Liu, Tokyo (JP)

(73) Assignees: NIKON CORPORATION;, Tokyo (JP); OPTOS PLC, Fife (GB)

(*) Notice: Subject to any disclaimer, the term of this patent is extended or adjusted under 35 U.S.C. 154(b) by 790 days.

(21) Appl. No.: 17/631,163

(22) PCT Filed: Jul. 29, 2020

(86) PCT No.: PCT/JP2020/029056
§ 371 (c)(1),
(2) Date: Feb. 2, 2022

(87) PCT Pub. No.: WO2021/020443
PCT Pub. Date: Feb. 4, 2021

(65) Prior Publication Data

US 2022/0301157 A1 Sep. 22, 2022

Related U.S. Application Data

(60) Provisional application No. 62/880,961, filed on Jul. 31, 2019.

(51) Int. Cl.
*G16H 50/20* (2018.01)
*G16H 30/20* (2018.01)
*G16H 30/40* (2018.01)

(52) U.S. Cl.
CPC ............ *G16H 50/20* (2018.01); *G16H 30/20* (2018.01); *G16H 30/40* (2018.01)

(58) Field of Classification Search
CPC ......... G16H 50/20; G16H 30/20; G16H 30/40
See application file for complete search history.

(56) References Cited

U.S. PATENT DOCUMENTS

2005/0086720 A1 4/2005 Shimizu et al.
2013/0136330 A1 5/2013 Takagi
(Continued)

FOREIGN PATENT DOCUMENTS

JP 2002-329190 A 11/2002
JP 2003-323496 A 11/2003
(Continued)

OTHER PUBLICATIONS

European Society of Radiology (ESR). What the radiologist should know about artificial intelligence—an ESR white paper. Insights Imaging 10, 44 (2019). (Year: 2019).*
(Continued)

*Primary Examiner* — Matthew L Hamilton
(74) *Attorney, Agent, or Firm* — Foley & Lardner LLP

(57) ABSTRACT

An information processing system comprises: an image acquisition device acquiring subject eye image data of a patient; a first information processing device storing the image data; a second information processing device obtaining the image data as a first diagnosis result using artificial intelligence; and a third information processing device obtaining the image data as a second diagnosis result by a radiologist, the image acquisition device: generates diagno-
(Continued)

sis method information indicating a diagnosis by artificial intelligence and/ or a radiologist; and transmits first transmission data including the image data and the diagnosis method information to the first information processing device, the first processing device: stores the image data when receiving the first transmission data from the image acquisition device; and transmits, based on the diagnosis method information, second transmission data including the image data to the second and/ or the third information processing.

14 Claims, 10 Drawing Sheets

(56) References Cited

U.S. PATENT DOCUMENTS

| | | | | |
|---|---|---|---|---|
| 2014/0068653 | A1 | 3/2014 | Ohta | |
| 2015/0172681 | A1 | 6/2015 | Kim et al. | |
| 2016/0034645 | A1 | 2/2016 | Takahashi et al. | |
| 2016/0360958 | A1* | 12/2016 | Tsuri | A61B 3/0025 |
| 2019/0189265 | A1 | 6/2019 | Stoval et al. | |
| 2019/0206054 | A1* | 7/2019 | Mao | G06T 7/0012 |
| 2019/0221313 | A1 | 7/2019 | Rim et al. | |
| 2020/0069175 | A1* | 3/2020 | Kumagai | A61B 3/0025 |
| 2020/0160521 | A1* | 5/2020 | Wang | G06V 10/82 |
| 2020/0288963 | A1* | 9/2020 | Lin | G16H 80/00 |
| 2020/0294655 | A1* | 9/2020 | Tahmasebi Maraghoosh | G16H 50/20 |
| 2021/0065899 | A1* | 3/2021 | Aladahalli | G16H 30/40 |

FOREIGN PATENT DOCUMENTS

| | | | |
|---|---|---|---|
| JP | 2014-048824 | A | 3/2014 |
| JP | 5951086 | B2 | 7/2016 |
| JP | 2018-014058 | A | 1/2018 |
| JP | 2018-139139 | A | 9/2018 |
| WO | WO-2012/046842 | A1 | 4/2012 |

OTHER PUBLICATIONS

International Search Report with English translation and Written Opinion issued in corresponding application No. PCT/JP2020/029056 dated Oct. 20, 2020.

CN Office Action issued in corresponding of Chinese Appl. Ser. No. 202080068976.6 dated Jun. 28, 2024 (20 pages).

Extended European Search Report issued in corresponding European Patent Application No. 20848394.1, dated Jul. 17, 2023 (9 pages).

JP Office Action for JP Appl. Ser. No. 2024-160478 dated Jun. 17, 2025 (6 pages).

* cited by examiner

310

3101 3102

| PATIENT INFORMATION | | | | | DIAGNOSIS HISTORY INFORMATION | | | |
|---|---|---|---|---|---|---|---|---|
| PATIENT ID | NAME | SEX | DOB | CONTACT | FIRST | ... | J-TH | ... |
| P1 | FN1 | S1 | DOB1 | AD1 | D11 | ... | D1j | ... |
| ⋮ | ⋮ | ⋮ | ⋮ | ⋮ | ⋮ | ⋮ | ⋮ | ⋮ |
| Pi | FNi | Si | DOBi | ADi | Di1 | ... | Dij | ... |
| ⋮ | ⋮ | ⋮ | ⋮ | ⋮ | ⋮ | ⋮ | ⋮ | ⋮ |

INFORMATION PROCESSING SYSTEM, INFORMATION PROCESSING DEVICE, IMAGE ACQUISITION DEVICE, INFORMATION PROCESSING METHOD, IMAGE ACQUISITION METHOD, AND PROGRAM

CROSS-REFERENCE TO RELATED APPLICATIONS

The present application is a national stage entry of PCT/JP2020/029056, filed on Jul. 29, 2020, which claims priority from U.S. provisional application 62/880,961 filed on Jul. 31, 2019, the contents of all of which are hereby incorporated by reference in their entirety.

TECHNICAL FIELD

The present invention relates to an information processing system, an information processing device, an image acquisition device, an information processing method, an image acquisition method, and a program.

BACKGROUND

A known ophthalmological information processing server can perform ophthalmological image analysis (see Patent Document 1). A system that provides more freedom when diagnosing is required.

PRIOR ART

Patent Document

[Patent Document 1] JP 5951086 B

SUMMARY OF THE INVENTION

An information processing system which is an aspect of the present invention disclosed in the present application comprises: an image acquisition device configured to acquire subject eye image data of a patient; a first information processing device which can communicate with the image acquisition device and which is configured to store the subject eye image data; a second information processing device which can communicate with the first information processing device and which is configured to obtain the subject eye image data as a first diagnosis result using artificial intelligence; and a third information processing device which can communicate with the first information processing device and which is configured to obtain the subject eye image data as a second diagnosis result by a radiologist, the image acquisition device performs: a first generation processing of generating diagnosis method information indicating a diagnosis using artificial intelligence and/or a diagnosis by a radiologist; and a first transmission processing of transmitting first transmission data including the subject eye image data and the diagnosis method information to the first information processing device, the first processing device performs: a storage processing of storing the subject eye image data when receiving the first transmission data from the image acquisition device; and a second transmission processing of transmitting, on the basis of the diagnosis method information, second transmission data including the subject eye image data to the second information processing device and/or the third information processing device.

A first information processing device which is an aspect of the present invention disclosed in the present application can communicate with an image acquisition device configured to acquire subject eye image data of a patient and stores the subject eye image data, the first information processing device comprises: a reception unit configured to receive first transmission data including the subject eye image data and diagnosis method information indicating whether image diagnosis is performed using artificial intelligence and/or by a radiologist, the first transmission data being transmitted from the image acquisition device; a generation unit configured to generate second transmission data including the subject eye image data; a control unit configured to determine a transmission destination of the second transmission data on the basis of the diagnosis method information output from a second information processing device that outputs a first diagnosis result after performing image diagnosis using artificial intelligence and from a third information processing device that outputs a second diagnosis result after performing image diagnosis by a radiologist; and a transmission unit configured to transmit the second transmission data to the transmission destination determined by the control unit.

An image acquisition device which is an aspect of the present invention disclosed in the present application can communicate with a first information processing device configured to store subject eye image data of a patient and acquires the subject eye image data, the image acquisition device comprises: an acquisition unit configured to acquire the subject eye image data; a generation unit configured to generate first transmission data including the subject eye image data and diagnosis method information indicating whether image diagnosis is performed using artificial intelligence and/or by a radiologist; and a transmission unit configured to transmit the first transmission data to the first information processing device.

A method for processing information which is an aspect of the present invention disclosed in the present application, the method is performed by a first information processing device, wherein the first information device can communicate with an image acquisition device configured to acquire subject eye image data of a patient and is configured to store the subject eye image data, the first information processing device, the method comprises: receiving, by the first information processing device, first transmission data including the subject eye image data and diagnosis method information indicating whether image diagnosis is performed using artificial intelligence and/or by a radiologist, the first transmission data being transmitted from the image acquisition device; generating, by the first information processing device, second transmission data including the subject eye image data; determining, by the first information processing device, a transmission destination of the second transmission data on the basis of the diagnosis method information output from a second information processing device that outputs a first diagnosis result after performing image diagnosis using artificial intelligence and from a third information processing device that outputs a second diagnosis result after performing image diagnosis by a radiologist; and transmitting, by the first information processing device, the second transmission data to the determined transmission destination.

A method for acquiring an image which is an aspect of the present invention disclosed in the present application, the method is performed by an image acquisition device, wherein the image acquisition device can communicate with a first information processing device configured to store subject eye image data of a patient and is configured to acquire the subject eye image data, the method comprises: acquiring, by the image acquisition device, the subject eye image data; generating, by the image acquisition device, first transmission data including the subject eye image data and diagnosis method information indicating whether image diagnosis is performed using artificial intelligence and/or by a radiologist; and transmitting, by the image acquisition device, the first transmission data to the first information processing device.

A computer program which is an aspect of the present invention disclosed in the present application causes a first information processing device to perform information processing, wherein the first information device can communicate with an image acquisition device configured to acquire subject eye image data of a patient and is configured to store the subject eye image data, the first information processing device, the program causes the first information device to: receive first transmission data including the subject eye image data and diagnosis method information indicating whether image diagnosis is performed using artificial intelligence and/or by a radiologist, the first transmission data being transmitted from the image acquisition device; generate second transmission data including the subject eye image data; determine a transmission destination of the second transmission data on the basis of the diagnosis method information output from a second information processing device that outputs a first diagnosis result after performing image diagnosis using artificial intelligence and from a third information processing device that outputs a second diagnosis result after performing image diagnosis by a radiologist; and transmit the second transmission data to the determined transmission destination.

A computer program which is an aspect of the present invention disclosed in the present application causes to an image acquisition device to perform image acquire processing, wherein the image acquisition device can communicate with a first information processing device configured to store subject eye image data of a patient and is configured to acquire the subject eye image data, the program causes the image acquisition device to: acquire the subject eye image data; generate first transmission data including the subject eye image data and diagnosis method information indicating whether image diagnosis is performed using artificial intelligence and/or by a radiologist; and transmit the first transmission data to the first information processing device.

BRIEF DESCRIPTIONS OF DRAWINGS

The present invention can be appreciated by the description which follows in conjunction with the following figures, wherein.

DETAILED DESCRIPTION OF THE PREFERRED EMBODIMENTS

Figure 1:
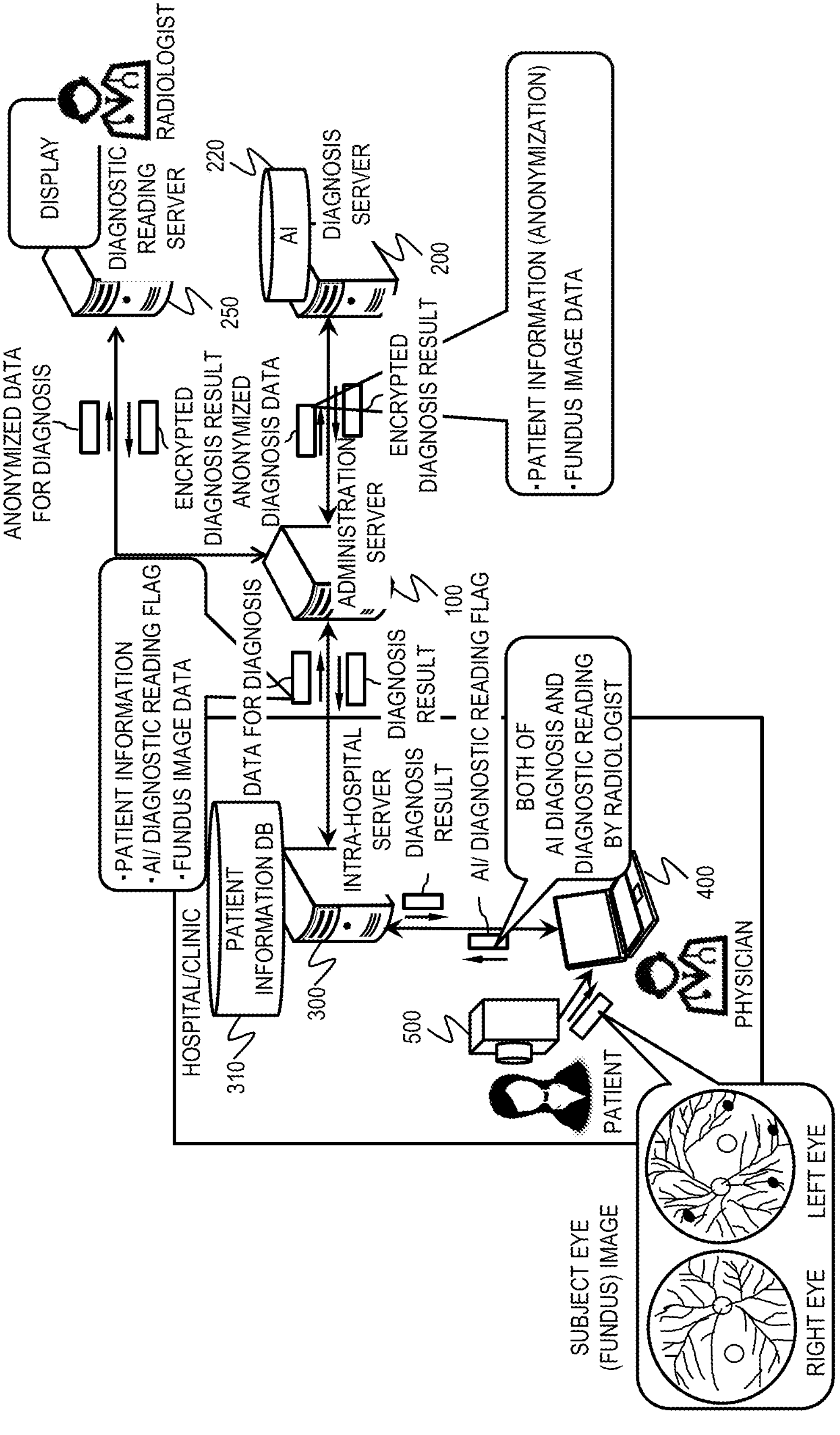
FIG. 1 is a diagram illustrating a configuration example of an image diagnosis system according to the first embodiment.

Hereinafter, embodiments of the invention are described in detail with reference to the accompanying drawings. It should be noted that the present embodiments are merely examples for implementing the present inventions, and do not limit the technical scope of the present inventions. In drawings, same components are denoted by same reference numerals in principle, and a repetitive description thereof is omitted.

First Embodiment

FIG. 1 is a diagram illustrating a configuration example of an image diagnosis system according to the present embodiment. The image diagnosis system includes an administration server 100, diagnosis server 200, and a diagnostic reading server 250. The image diagnosis system also includes, for example, an intra-hospital server 300 installed in a hospital, clinic or other diagnostic facility, a terminal 400, and an imaging device 500. The intra-hospital server 300, the terminal 400, and the imaging device 500 are connected to each other via a network.

The fundus image data may be any one of fundus image data captured by a fundus camera, fundus image data of a fundus captured by a scanning laser ophthalmoscope, or tomographic data of a fundus captured by an optical coherence tomography machine. Alternatively, the fundus image data may be a fundus image dataset comprised of a combination of two or more of the above-described types of data. The imaging device 500 may image an anterior section of a subject eye as well as the fundus and generate anterior eye image data. The fundus image data and the anterior eye image data are examples of patient eye image data.

The terminal 400 is an example of an image acquisition device and is a computer such as a personal computer (PC) or a tablet used by a physician requesting the diagnosis or an operator of an ophthalmological device. The terminal 400 sends AI/diagnostic reading information, patient information, and fundus image data to the intra-hospital server 300. The AI/diagnostic reading information is information used to indicate a diagnosis method that is one or both of diagnosis using the AI 220 in the diagnosis server 200, which is a first requester server and diagnosis by a radiologist in a facility where the diagnostic reading server 250, which is a second requester server, is installed.

The AI/diagnostic reading information may be held as an AI/diagnostic reading flag (01: image diagnosis using AI, 10: image diagnosis by radiologist, 11: image diagnosis using both AI and diagnostic reading). The AI/diagnostic reading information is also request destination designation information used to designate a request destination for either image diagnosis when the requester is AI, image diagnosis when the requester is a radiologist, or image diagnosis when the requester is both AI and a radiologist. The same applies to the AI/diagnostic reading flag, which can also function as a request destination designation information flag.

The intra-hospital server 300 is an example of an image acquisition device. The intra-hospital server 300 includes a patient information database (DB) 310 that holds patient information and stores the acquired patient information in the patient information DB 310. The intra-hospital server 300 is connected to the administration server 100 via a network. The intra-hospital server 300 creates data for diagnosis, which is an example of first transmission data, by making a set of the patient information, the fundus image data and the AI/diagnostic reading information received from the terminal 400. Then, the intra-hospital server 300 sends the data for diagnosis to the administration server 100. Some or all of the patient information in the data for diagnosis and the AI/diagnostic reading information may be generated by the intra-hospital server 300. Further, the fundus image data captured by the imaging device 500 may be stored in the patient information DB 310.

The administration server 100 is an example of a first information processing device and generates anonymized data for diagnosis (example of second transmission data) obtained by anonymizing some information (e.g., patient information) in the data for diagnosis received from the intra-hospital server 300. The administration server 100 is connected to the diagnosis server 200 and the diagnostic reading server 250 via a network. The administration server 100 selects the diagnosis server 200 and/or the diagnostic reading server 250 as a request destination (transmission destination) for the fundus image data based on the AI/diagnostic reading information and sends the anonymized data for diagnosis to the selected server.

The administration server 100 receives an image diagnosis result from the diagnosis server 200 and/or the diagnostic reading server 250 and sends this result to the intra-hospital server 300 and the terminal 400. The function of storing the fundus image data may be given to an image DB (not shown) in the administration server 100 instead of the intra-hospital server 300. A small clinic may not have an intra-hospital server and, in that case, the administration server 100 may have the function of the intra-hospital server 300.

If the AI/diagnostic reading information is an AI/diagnostic reading flag generated by the intra-hospital server 300 or the terminal 400, the administration server 100 determines the transmission destination server for the anonymized data for diagnosis according to the AI/diagnostic reading flag.

The diagnosis server 200 is an example of a second information processing device and is equipped with artificial intelligence (AI) 220 that performs image diagnosis on the fundus image data. After receiving the anonymized data for diagnosis, the diagnosis server 200 performs image diagnosis using the AI 220 on fundus image data included in the anonymized data for diagnosis and sends an encrypted diagnosis result to the administration server 100. The AI 220 includes an AI that can determine the symptom level of a particular disease such as diabetic retinopathy and an AI that can determine the onset of symptoms of one or more types of diseases.

The diagnostic reading server 250 is an example of a third information processing device and is, for example, a server installed in a diagnostic reading facility with a radiologist. After receiving the anonymized data for diagnosis, the diagnostic reading server 250 displays a fundus image included in the anonymized data for diagnosis on a display or other device and accepts input of a diagnosis result for the fundus image data determined by the radiologist. The diagnostic reading server 250 encrypts the input diagnosis result and sends the encrypted diagnosis result to the administration server 100.

Devices included in the image diagnosis system may be connected to each other. The function of each device included in the image diagnosis system may be partly or entirely included in or integrated with another device. Specifically, for example, the terminal 400 and the imaging device 500 may be integrated and the intra-hospital server 300 and the terminal 400 may be integrated.

To facilitate explanation, one diagnosis server 200 and one diagnostic reading server 250 are illustrated in FIG. 1, but the image diagnosis system may include a plurality of diagnosis servers 200 and a plurality of diagnostic reading servers 250. In other words, in this case, the administration server 100 may request an image diagnosis from one or more selected diagnosis servers 200 and/or one or more selected diagnostic reading servers 250.

Figure 2:
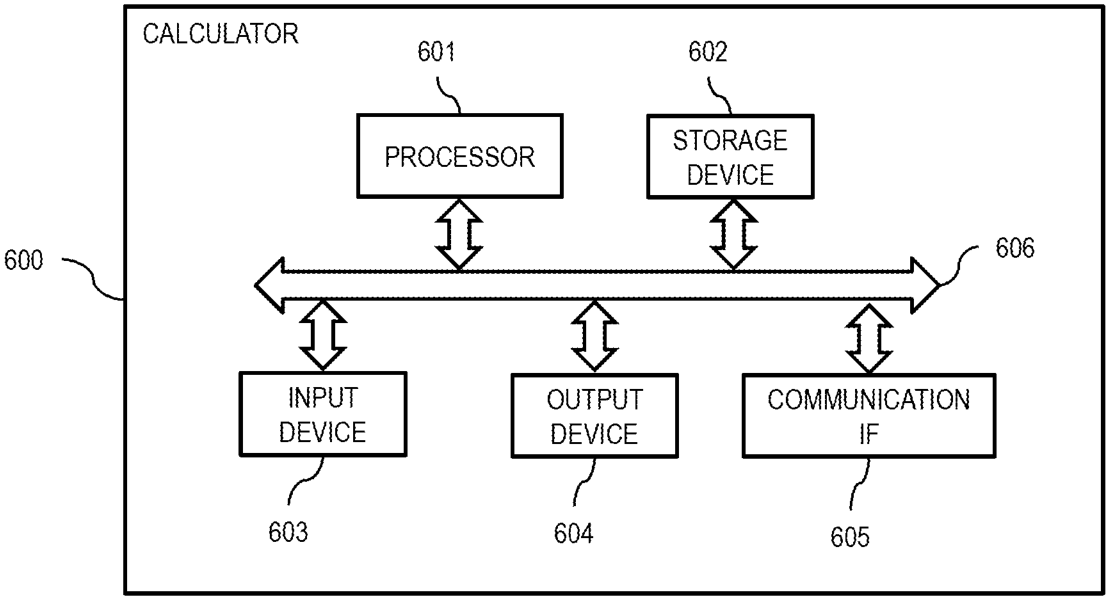
FIG. 2 is a block diagram illustrating hardware configuration examples of computers according to the first embodiment.

FIG. 2 is a block diagram illustrating hardware configuration examples of computers constituting the administration server 100, the diagnosis server 200, a diagnostic reading server 250, the intra-hospital server 300, and the terminal 400. A computer 600 includes, for example, a processor (CPU) 601, a storage device 602, an input device 603, an output device 604, and a communication interface (IF) 605. These components are connected to each other via internal signal wiring 606.

The processor 601 executes a program stored in the storage device 602. The storage device 602 includes a memory. This memory incudes a ROM as a non-volatile storage element and a RAM as a volatile storage element. The ROM stores firmware (e.g., a BIOS). The RAM is a high-speed and volatile storage element such as a dynamic random-access memory (DRAM) and temporarily stores programs executed by the processor 601 and data used when executing the programs.

The storage device 602 includes an auxiliary storage device. This auxiliary storage device is a large-capacity and non-volatile storage device such as a magnetic storage device (HDD) or a flash memory (SSD), and stores programs executed by the processor 601 and data used when executing the programs. More specifically, the programs are read out from the auxiliary storage device, loaded to the memory and executed by the processor 601.

The input device 603 is an interface such as a keyboard or mouse that receives input from an operator. The output device 604 is a device such as a display or a printer that outputs an execution result of the program in a format recognizable by the operator. The input device 603 and the output device 604 may be formed integrally, such as in a touch-panel device. The communication I/F 605 is a network interface device that controls communication with other devices according to predetermined protocols.

The program to be executed by the processor 601 is provided to the computer 600 via a removable medium (CD-ROM, flash memory, etc.) or a network and stored in the non-volatile auxiliary storage device, which is an example of a permanent storage medium. Thus, the computer 600 preferably includes an interface configured to read data from a removable medium.

The administration server 100, the diagnosis server 200, a diagnostic reading server 250, the intra-hospital server 300, and the terminal 400 are all computer systems physically configured on one computer 600 or theoretically or physically configured on a plurality of computers 600, and may operate on separate threads on the same computer 600 or operate on a virtual computer built on a plurality of physical computer resources.

Figure 3:
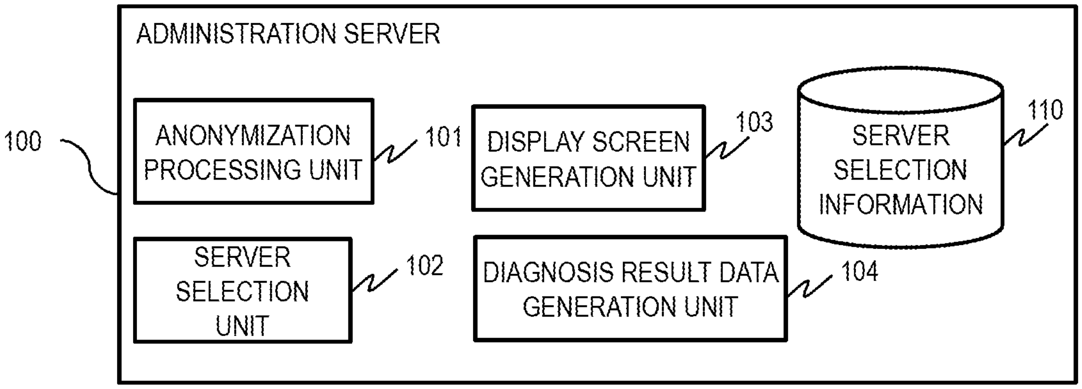
FIG. 3 is a block diagram illustrating a functional configuration example of an administration server according to the first embodiment.

FIG. 3 is a block diagram illustrating a functional configuration example of the administration server 100. The administration server 100 includes an anonymization processing unit 101, a server selection unit 102, a display screen generation unit 103, and a diagnosis result data generation unit 104. The anonymization processing unit 101 anonymizes the patient information included in the data for diagnosis sent from the intra-hospital server 300. The server selection unit 102 selects as a transmission destination (request destination of image diagnosis) for the data for diagnosis based on the AI/diagnostic reading information included in the data for diagnosis.

The display screen generation unit 103 generates screen information displayed on the output device 604. The diagnosis result data generation unit 104 decrypts the encrypted diagnosis result received from the diagnosis server, generates a display screen displaying the diagnosis result and sends information on this display screen to the intra-hospital server 300.

The functional units in the administration server 100 are realized by a processor 601 in the computer 600 configured to operate the administration server 100. Specifically, the processor 601 operates according to an anonymization processing program stored in a memory in the storage device 602 to function as the anonymization processing unit 101, and operates according to an AI selection program stored in a memory in the storage device 602, to function as the AI selection unit 102. The same applies to other functional units in the administration server 100 and other devices, where the processor 601 operates according to programs loaded into memories.

The administration server 100 holds the server selection information 110. The server selection information 110 is information configured as, for example, a lookup table and indicates correspondence between the request destination server (diagnosis server 200 and/or diagnostic reading server 250) that performs the image diagnosis and the AI/diagnostic reading information. If the transmission destination server for the anonymized data for diagnosis is determined by the terminal 400 or the intra-hospital server 300, the administration server 100 may not hold the server selection information 110.

The server selection information 110 is stored in an auxiliary storage device included in the storage device 602 of the calculator 600 that realizes the functions of the administration server 100. The same applies to information and DB held by another device. In other words, such information is stored in an auxiliary storage device included in the storage device 602 of the calculator 600 that realizes the functions of the other device.

In the present embodiment, information used by each device included in the image diagnosis system may be represented by any data structure regardless of the data structure. For example, a data structure appropriately selected from a table, a list, a database or a queue may store the information.

Figure 4:
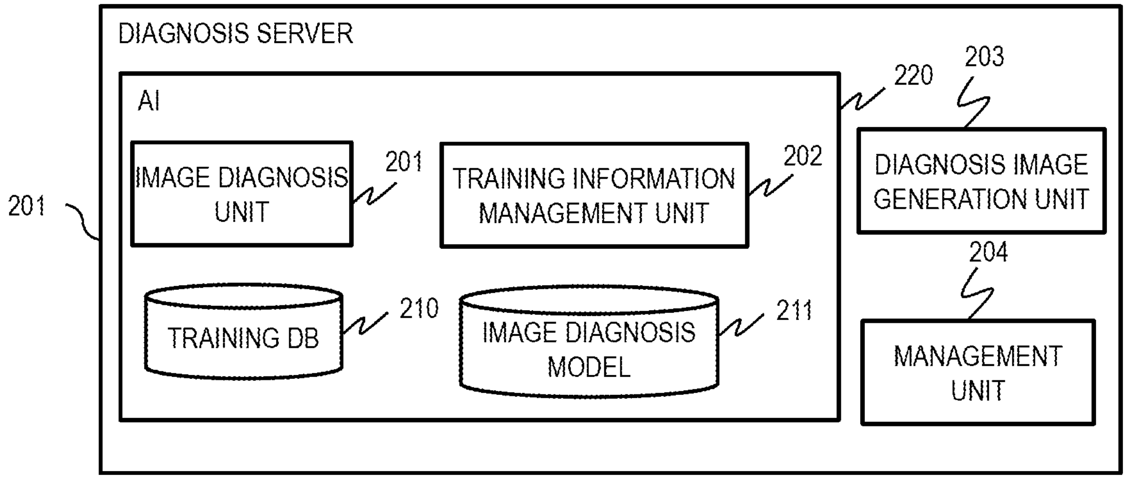
FIG. 4 is a block diagram illustrating a functional configuration example of a diagnosis server according to the first embodiment.

FIG. 4 is a block diagram illustrating a functional configuration example of the diagnosis server 200. The diagnosis server 200 includes an image diagnosis unit 201, a training information management unit 202, a diagnosis image generation unit 203, and a management unit 204. The diagnosis server 200 holds a training DB 210 and an image diagnosis model 211. The training DB 210 is a database used for building the image diagnosis model 211. The image diagnosis model 211 is a model that outputs a diagnosis result when fundus image data is input.

The AI 220 is realized by the image diagnosis unit 201, the training information management unit 202, the training DB 210, and the image diagnosis model 211. The image diagnosis unit 201 performs, for example, image diagnosis for diabetic retinopathy to determine a grade of diabetic retinopathy by using the image diagnosis model 211 on the fundus image data included in the anonymized data for diagnosis received from the administration server 100.

The training information management unit 202 stores the fundus image data and the image diagnosis result included in the anonymized data for diagnosis in the training DB 210 as training data for the AI to update the training DB 210. The training information management unit 202 updates (e.g., optimizes) the image diagnosis model 211 through training based on the updated training DB 210.

The diagnosis image generation unit 203 generates a diagnosed fundus image in which information including a mark indicating the location of an abnormality and the name of a disease are superimposed on the diagnosed fundus image. The management unit 204 manages versions and updates of the AI 220. The management unit 204 also creates a package of the grade of diabetic retinopathy and the diagnosed fundus image (when created by the diagnosis image generation unit 203) as the diagnosis result. Then, the management unit 204 associates the diagnosis result and the anonymized patient information to generate AI diagnosis result information. The generated AI diagnosis result information is sent to the administration server 100.

The diagnosis server 200 may or may not include a training function for the image diagnosis model 211. In other words, the diagnosis server 200 may continue to perform image diagnosis with a preset and fixed image diagnosis model 211 without updating the image diagnosis model 211. In this case, the diagnosis server 200 may or may not include the training information management unit 202 and the training DB 210.

Figure 5:
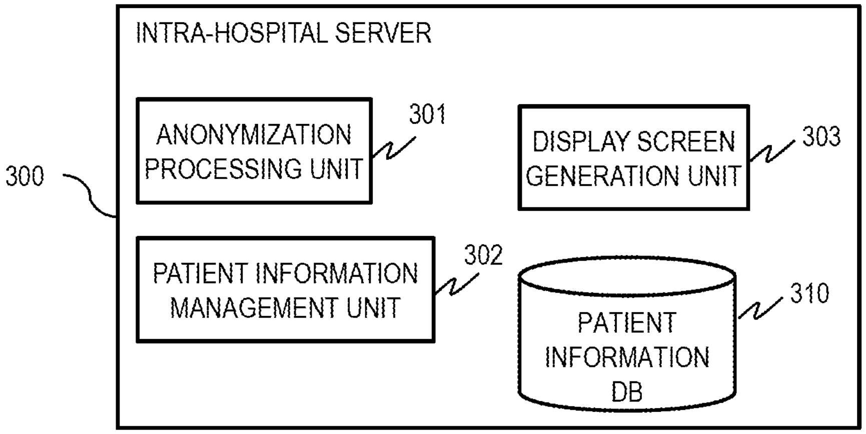
FIG. 5 is a block diagram illustrating a functional configuration example of an intra-hospital server according to the first embodiment.

FIG. 5 is a block diagram illustrating a functional configuration example of the intra-hospital server 300. The intra-hospital server 300 includes, for example, the anonymization processing unit 301, the patient information management unit 302, and the display screen generation unit 303. The intra-hospital server 300 holds a patient information DB 310. The intra-hospital server 300 may hold the server selection information and, in this case, the intra-hospital server 300 may use the server selection information to determine the transmission destination of the anonymized diagnosis data.

The anonymization processing unit 301 anonymizes the patient information included in the data for diagnosis. The patient information management unit 302 stores the patient information included in the data for diagnosis in the patient information DB 310, acquires the patient information from the patient information DB 310 and adds to the data for diagnosis. The display screen generation unit 303 generates screen information to be displayed on the output device 604. The patient information DB 310 holds personal information and diagnosis history information of the patient.

If the intra-hospital server 300 includes the server selection information, the server selection information is configured as, for example, a lookup table and indicates correspondence between the AI/diagnostic reading information and the server (diagnosis server 200 and/or diagnostic reading server 250), similar to the server selection information 110 in the administration server 100.

Figure 6:
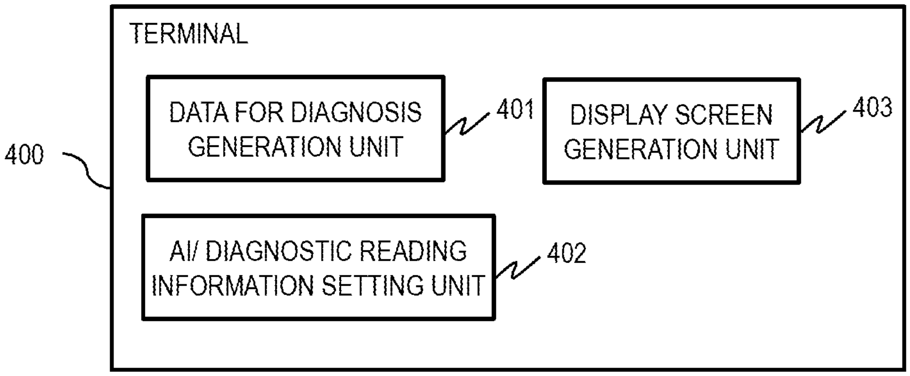
FIG. 6 is a block diagram illustrating a functional configuration example of a terminal according to the first embodiment.

FIG. 6 is a block diagram illustrating a functional configuration example of the terminal 400. The terminal 400 includes a data for diagnosis generation unit 401, an AI/diagnostic reading information configuration unit 402, and a display screen generation unit 403. The data for diagnosis generation unit 401 generates data for diagnosis including the patient information, additional information, and the fundus image data. The AI/diagnostic reading information configuration unit 402 acquires information used for selecting the server that performs image diagnosis. The display screen generation unit 403 generates screen information to be displayed on the output device 604.

The terminal 400 may hold the server selection information and, in this case, the terminal 400 may use the server selection information to determine the transmission destination server for the anonymized data for diagnosis. The server selection information held by the terminal 400 is similar to the server selection information 110 and, for example, indicates correspondence between the AI/diagnostic reading information and the server (diagnosis server 200 and/or diagnostic reading server 250). The terminal 400 may hold the server selection information and, in this case, the terminal 400 may use the server selection information to determine the transmission destination for the anonymized data for diagnosis.

When the terminal 400 includes the server selection information, the server selection information is configured as, for example, a lookup table and indicates correspondence between the AI/diagnostic reading information and the server (diagnosis server 200 and/or diagnostic reading server 250), similar to the server selection information 110 in the administration server 100.

Figure 7:
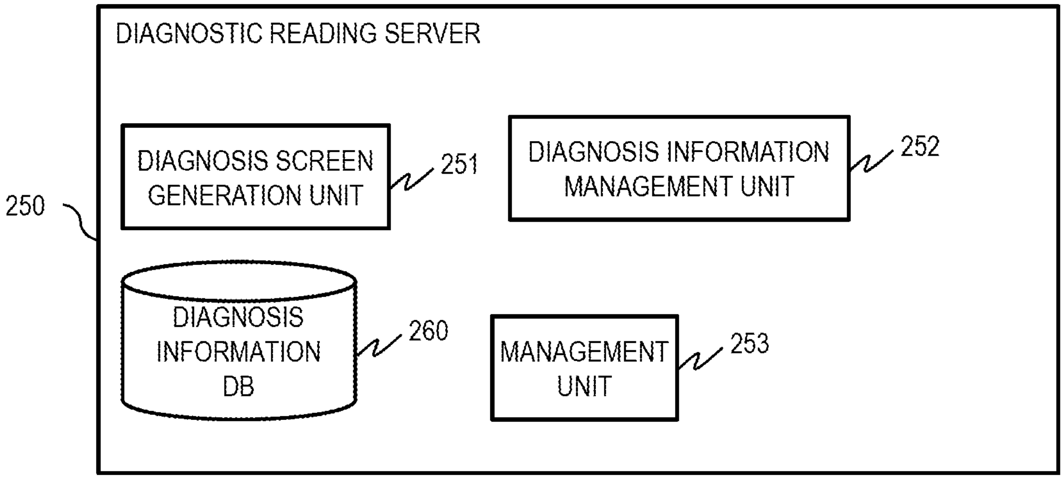
FIG. 7 is a block diagram illustrating a functional configuration example of a diagnostic reading server according to the first embodiment.

FIG. 7 is a block diagram illustrating a functional configuration example of the diagnostic reading server 250. The diagnostic reading server 250 includes, for example, a diagnosis screen generation unit 251, a diagnosis information management unit 252, and a management unit 253. The diagnostic reading server 250 holds a diagnosis information DB 260 that stores a collection of diagnostic cases.

The diagnosis screen generation unit 251 generates a diagnosis screen based on an instruction from a radiologist at a diagnostic reading facility including the diagnostic reading server 250 by using the fundus image data in the data for diagnosis sent from the administration server 100 and anonymized patient information (patient information such as sex and age needed by the radiologist to make a diagnosis and that does not identify the individual). Then, the generated diagnosis screen data is displayed on a display (not shown). The radiologist interprets the fundus image on the diagnosis screen and determines the grade of diabetic retinopathy (the radiologist may further discover another disease).

Then, the radiologist inputs the grade of diabetic retinopathy into a diagnosis result input field on the diagnosis screen. The radiologist may further input their findings and findings related to another discovered disease in a comment field. Further, a mark or text may be input on the displayed fundus image. The diagnosis screen generation unit 251 may be configured to display data of a collection of diagnostic cases on a display to refer to this data based on a request by the radiologist.

The diagnosis information management unit 252 creates a package of image data of the grade of diabetic retinopathy input, text input by the radiologist and the fundus image written on by the radiologist via the diagnosis screen as a diagnosis result. Then, the management unit 253 associates information related to the radiologist who interpreted the data (name or code identifying radiologist), the diagnosis result and the anonymous patient information to generate radiologist diagnosis result information. Then, the radiologist diagnosis result information is sent to the administration server 100.

Figure 8:
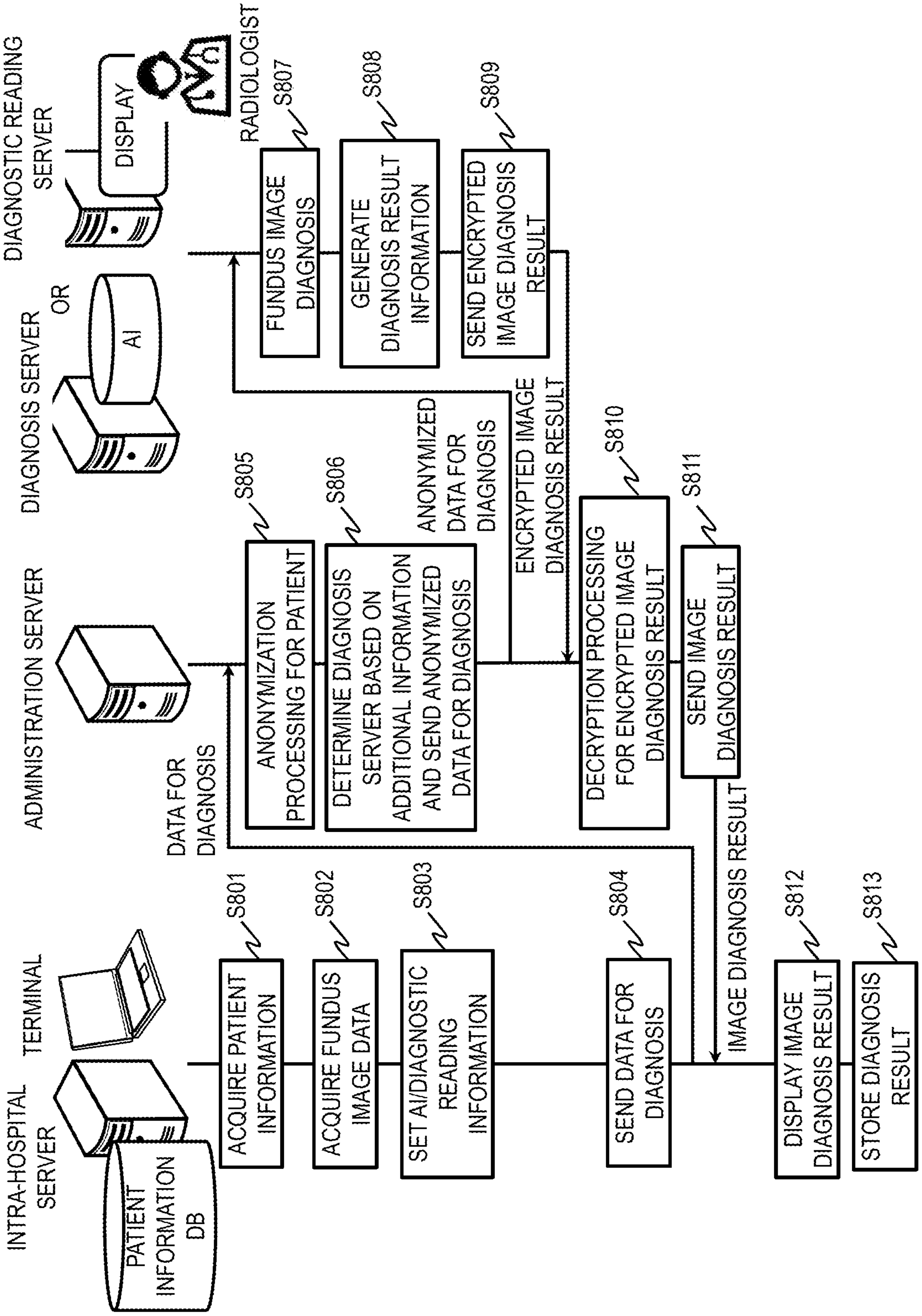
FIG. 8 is a sequence diagram illustrating an example of image diagnosis processing according to the first embodiment.

FIG. 8 is a sequence diagram illustrating an example of image diagnosis processing. In FIG. 8, the server that performs image diagnosis is selected based on the AI/diagnostic reading information.

First, the data for diagnosis generation unit 401 of the terminal 400 receives input of patient information via the input device 603 (S801). Information such as an ID that identifies the patient, name, sex, address, medical history, medication history and examination results are all examples of patient information. For a patient for which information is already registered in the patient information DB 310, the data for diagnosis generation unit 401 need only receive input of an ID that identifies the patient and acquire other information from registered information corresponding to that ID.

The data for diagnosis generation unit 401 acquires subject eye image data for both eyes of the patient that is sent from the imaging device 500 (S802). In the present embodiment, the fundus image data for both eyes may be acquired or fundus image data for either the left eye or the right eye may be acquired. The data for diagnosis generation unit 401 generates a left/right eye flag indicating whether the fundus image data is data for both eyes, data for only the right eye, or data for only the left eye. The data for diagnosis generation unit 401 may acquire fundus image data from a device other than the imaging device 500.

Then, the AI/diagnostic reading information configuration unit 402 configures the AI/diagnostic reading information (S803). The AI/diagnostic reading information configuration unit 402 may set the AI/diagnostic reading flag as the AI/diagnostic reading information, or the administration server 100 may collect information necessary for determining the transmission destination server as the AI/diagnostic reading information. Details of the Step S803 will be described later.

Then, the data for diagnosis generation unit 401 sends the data for diagnosis including the patient information, the left/right eye flag, the fundus image data, and the AI/diagnostic reading information to the administration server 100 via the intra-hospital server 300 (S804). The patient information management unit 302 of the intra-hospital server 300 stores the patient information received from the terminal 400 in the patient information DB 310.

If the patient information received from the terminal 400 is insufficient, the patient information management unit 302 may reference the patient information DB 310 to acquire patient information and supplement the data for diagnosis. Specifically, if, for example, the patient information received from the terminal 400 is only the ID that identifies the patient, the patient information management unit 302 acquires patient information corresponding to the ID from the patient information DB 310 and sends data for diagnosis including the acquired patient information to the administration server 100.

Then, the anonymization processing unit 101 of the administration server 100 performs anonymization processing using a predetermined algorithm on the patient information and diagnosis history information included in the received data for diagnosis (S805). As the anonymization processing, the anonymization processing unit 101 performs processing of anonymizing the patient ID (replacing the patient ID with an ID unique to the fundus image data) and deleting personal information of the patient, such as name and name of disease. The anonymization processing unit 101 may anonymize only part of the patient information and diagnosis history information (for example, sensitive information related to privacy). The anonymization processing for the patient information may be performed in advance by, for example, the anonymization processing unit 301 of the intra-hospital server 300 before the data for diagnosis is sent to the administration server 100.

The server selection unit 102 of the administration server 100 selects at least one of the diagnosis server 200 and the diagnostic reading server 250 based on the AI/diagnostic reading information (e.g., the AI/diagnostic reading flag) included in the received data for diagnosis and sends the anonymized data for diagnosis including the anonymized patient information the subject eye image data, and the AI/diagnostic reading information to the selected diagnosis server 200 (S806).

The server selection unit 102 may encrypt the anonymized data for diagnosis using an encryption key and send the encrypted data for diagnosis to the selected server. In this case, the diagnosis server 200 and/or diagnostic reading server 250 includes a decryption key corresponding to the above-described encryption key and decrypts the anonymized data for diagnosis with the encryption key in Step S807 to be described later.

Then, the diagnosis server 200 and/or diagnostic reading server 250 that has received the anonymized data for diagnosis starts a process of performing image diagnosis on the fundus image data included in the received anonymized data for diagnosis (S807). If the diagnosis server 200 receives the anonymized data for diagnosis. The image diagnosis unit 201 uses the image diagnosis model 211 to perform image diagnosis. In this case, the image diagnosis unit 201 may use the anonymized patient information and left/right eye flag for diagnosis by AI in the image diagnosis.

If the diagnostic reading server 250 receives anonymized data for diagnosis, the diagnosis information management unit 252 may send diagnosis information including the subject eye image data and the input diagnosis result to the diagnosis server 200 via the administration server 100, for example. In this case, the learning information management unit 202 of the diagnosis server 200 stores the subject eye image data in the learning DB 210 as learning data to update the learning DB 210 and update the image diagnosis model 211 based on the updated learning DB 210. As a result, the AI 220 of the diagnosis server 200 can learn even if the diagnosis server 200 is not requested to perform image diagnosis.

If the diagnostic reading server 250 receives the anonymized data for diagnosis, the diagnosis screen generation unit 251 displays the anonymized patient information, the left/right eye flag, and the subject eye image data on the display device 604 (display) of the diagnostic reading server 250. The diagnosis screen generation unit 251 of the diagnostic reading server 250 receives input of an image diagnosis result from the user (e.g., a radiologist) of the via the input device 603.

The diagnosis server 200 and/or diagnostic reading server 250 that performs fundus image diagnosis generates diagnosis result information. Specifically, when the diagnosis server 200 performs the fundus image diagnosis in Step S807, the diagnosis screen generation unit 203 generates the diagnosed fundus image (example of a first diagnosis result) in which information including a mark indicating the location of an abnormality and the name of a disease are superimposed on the diagnosed fundus image.

When the diagnostic reading server 250 starts the process for image diagnosis in Step S807, the diagnosis information management unit 252 creates a package of image data of the grade of diabetic retinopathy input, text input by the radiologist and the fundus image written on by the radiologist via the diagnosis screen as a diagnosis result. The management unit 253 associates the information related to the radiologist who interpreted the data (name or code identifying radiologist), the diagnosis result and the anonymous patient information to generate radiologist diagnosis result information (example of a second diagnosis result).

Then, the diagnosis server 200 and/or diagnostic reading server 250 that generated the image diagnosis result uses the encryption key held in the diagnosis server 200 and/or diagnostic reading server 250 to encrypt the image diagnosis result (if the diagnosis server 200 performs the diagnosis, this is the diagnosed fundus image, and if the radiologist performs the diagnosis with the diagnostic reading server 250, this is radiologist diagnosis result information (name of diagnosed disease, grade of symptoms, radiologist findings, etc.)), generates an encrypted image diagnosis result, and sends encrypted image diagnosis result to the administration server 100 (S809). In Step S809, anonymization may be performed in place of or in addition to encryption.

Next, the diagnosis result data generation unit 104 of the administration server 100 uses the decryption key in the administration server 100 to decrypt the received encrypted image diagnosis result (S810). If the received encrypted image diagnosis result has been anonymized, the diagnosis result data generation unit 104 restores the anonymized image diagnosis result patient information. Then, the diagnosis result data generation unit 104 associated the restored image diagnosis result with patient information related to the patient before anonymization.

Next, the diagnosis result data generation unit 104 generates a display screen (FIGS. 13 and 14 to be described later) indicating a diagnosis result, which is a grade of diabetic retinopathy as a diagnosis result, associates the display screen that displays the diagnosis result with the patient ID, and stores this information in a memory (not shown).

If, for example, the administration server 100 doesn't receive the encrypted image diagnosis result from the server that sent the anonymized data for diagnosis after a predetermined period of time has passed, data for anonymization may be sent to another server and that server may be requested to perform image diagnosis.

Next, the diagnosis result data generation unit 104 associates the decrypted image diagnosis result with patient information related to the patient before anonymization and sends this information to the intra-hospital server 300 (S811). The display screen generation unit 303 of the intra-hospital server 300 displays a display screen based on the received image diagnosis result and the patient information on the output device 604 of the intra-hospital server 300 (S812). The terminal 400 may acquire the image diagnosis result and the patient information from the intra-hospital server 300 and the display screen generation unit 403 of the terminal 400 may display a display screen based on the image diagnosis result and the patient information on the output device 604 of the terminal 400.

Further, the display screen generation unit 103 of the administration server 100 may generate information for the display screen based on the image diagnosis result and the patient information and send that information to the intra-hospital server 300, and the intra-hospital server 300 and the terminal 400 may display the display screen according to the generated information.

Next, the patient information management unit 302 stores diagnosis history information indicating decrypted image diagnosis result and which server performed the image diagnosis in the patient information DB 310 (S813).

Figure 9:
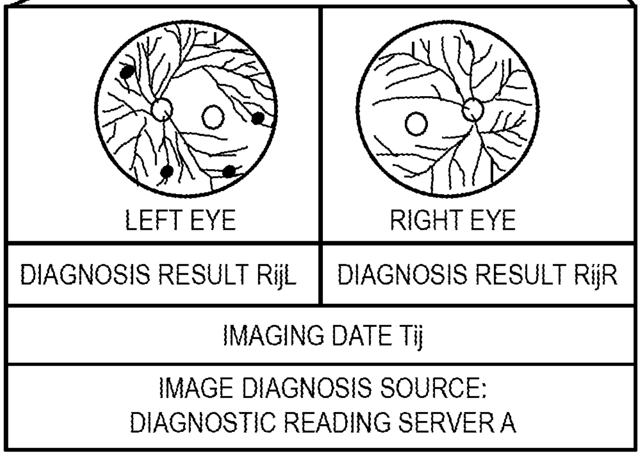
FIG. 9 illustrates an example of patient information DB according to the first embodiment.

FIG. 9 illustrates an example of the patient information DB 310. The patient information DB 310 includes a patient information field 3101 and a diagnosis history information field 3102. Information such as personal information related to each patient is stored in the patient information field 3101. Diagnosis history of the fundus image data by the diagnosis server 200 and the diagnostic reading server 250 is stored in the diagnosis history information field 3102. In the example of FIG. 8, identification information related to the fundus image data, the diagnosis result, the imaging date of the fundus image, and the diagnosis server 200 and/or diagnostic reading server 250 is recorded as the diagnosis history.

The setting processing for AI/diagnostic reading information in Step S803 will now be described in detail. The example described below deals with a case where, in Step S803, the AI/diagnostic reading information setting unit 402 of the terminal 400 sets the AI/diagnostic reading flag as the AI/diagnostic reading information. In this case, the administration server 100 determines the transmission destination of the fundus image data according to the AI/diagnostic reading flag.

Figure 10:
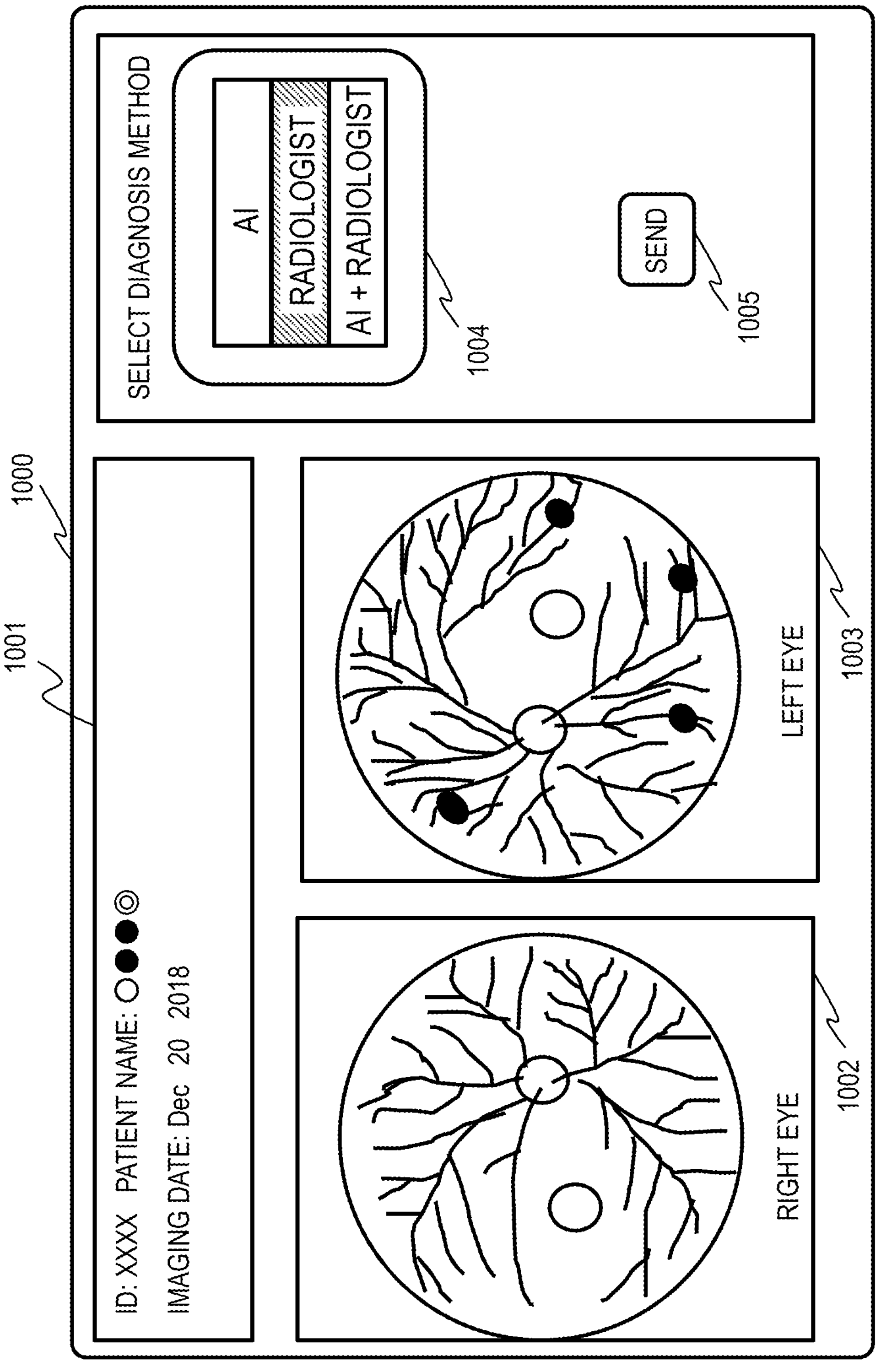
FIG. 10 illustrates an example of an input screen used to set the AI/diagnostic reading flag according to the first embodiment.

The AI/diagnostic reading information setting unit 402 directly receives configuration of the AI/diagnostic reading flag via the input device 603 and the communication IF 605. FIG. 10 illustrates an example of an input screen used to set the AI/diagnostic reading flag. The input screen 1000 includes a patient information display area 1001, a left eye image display area 1002, a right eye image display area 1003, a diagnosis method selection area 1004, and a transmission button 1005.

In the patient information display area 1001, information related to the patient such as an ID that identifies the patient and information related to the subject eye image such as the imaging date of the subject eye image are displayed. In the left eye image display area 1002, for example, a subject eye image of the left eye is displayed. In the right eye image display area 1003, for example, a subject eye image of the right eye is displayed.

The diagnosis method selection area 1004 is an area for selecting the AI/diagnostic reading flag. In the diagnosis method selection area 1004, when "AI" is selected, an AI/diagnostic reading flag "01" indicating the diagnosis server 200 is selected, when "radiologist" is selected, an AI/diagnostic reading flag "10" indicating the diagnostic reading server 250 is selected, and when "AI +radiologist" is selected, an AI/diagnostic reading flag "11" indicating the diagnosis server 200 and the diagnostic reading server 250 is selected.

In the example of FIG. 10, "radiologist" is selected in the diagnosis method selection area 1004, that is, the AI/diagnostic reading flag "10" indicating the diagnostic reading server 250 is selected. When the transmission button 1005 is selected, the AI/diagnostic reading flag selected in the diagnosis method selection area 1004 is set. With this configuration, the user of the terminal 400 can perform image diagnosis using a desired server.

If the terminal 400 holds the server selection information, the AI/diagnostic reading information setting unit 402 may acquire predetermined information in Step S803 and set the AI/diagnostic reading flag indicating the transmission destination server corresponding to the acquired information in the server selection information held by the terminal 400. The diagnosis history information of the patient indicated by the patient information DB 310 of the intra-hospital server 300 is an example of the predetermined information.

Figure 11:
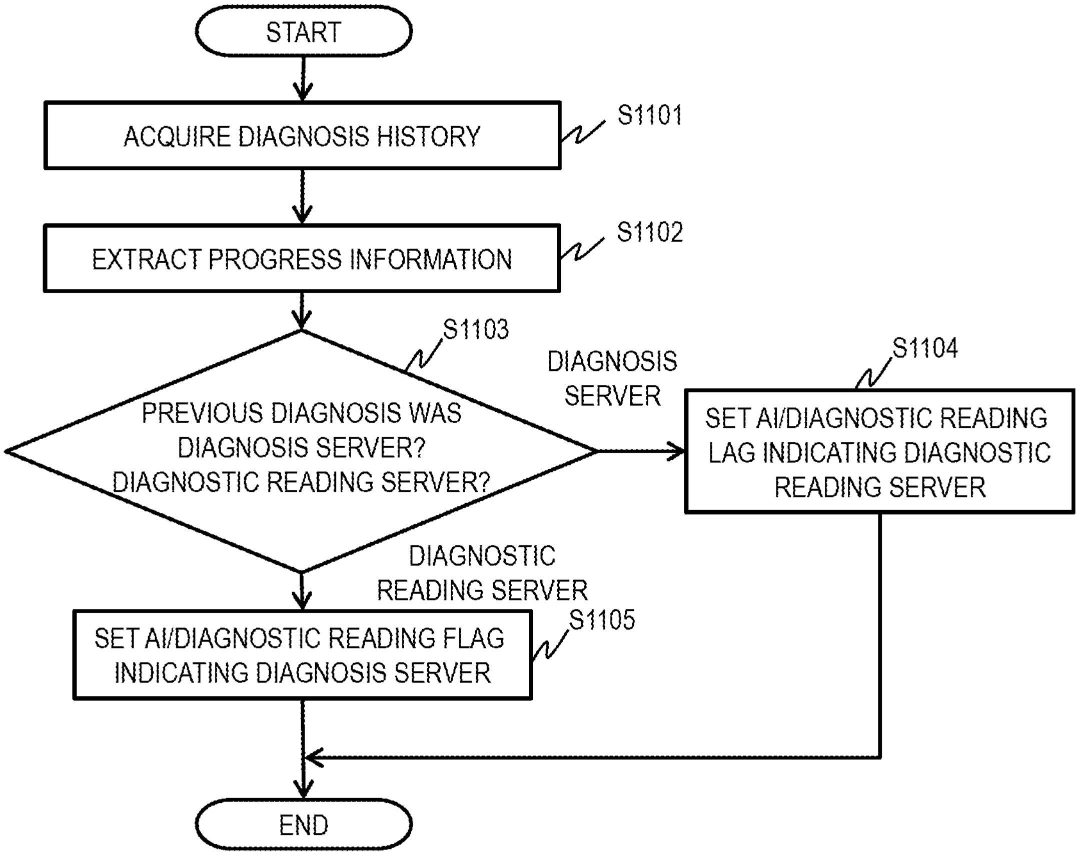
FIG. 11 is a flowchart illustrating an example of setting processing for the AI/diagnostic reading flag according to the first embodiment.

FIG. 11 is a flowchart illustrating an example of setting processing for the AI/diagnostic reading flag in Step S803 in such a case. First, the AI/diagnostic reading information setting unit 402 acquires diagnosis history of the patient from the patient information DB 310 of the intra-hospital server 300 as the AI/diagnostic reading information (S1101).

The AI/diagnostic reading information setting unit 402 extracts progress information of the acquired diagnosis history (S1102). Specifically, for example, the AI/diagnostic reading information setting unit 402 acquires most recent diagnosis information of the acquired diagnosis history.

Then, the AI/diagnostic reading information setting unit 402 determines whether the image diagnosis source in the most recent diagnosis information is the diagnosis server 200 or the diagnostic reading server 250 (S1103). If the AI/diagnostic reading information setting unit 402 determines that the image diagnosis source in the most recent diagnosis information is the diagnosis server 200 (S1103: Diagnosis server), the AI/diagnostic reading information setting unit 402 sets the AI/diagnostic reading flag indicating the diagnostic reading server 250 (S1104) and ends the processing in Step S802.

If the AI/diagnostic reading information setting unit 402 determines that the image diagnosis source in the most recent diagnosis information is the diagnostic reading server 250 (S1003: Diagnostic reading server), the AI/diagnostic reading information setting unit 402 sets the AI/diagnostic reading flag indicating the diagnosis server 200 (S1005) and ends the processing in Step S802.

In the example of FIG. 10, the AI/diagnostic reading flag is determined from one piece of the most recent diagnosis history, but a plurality of pieces or all pieces of the most recent diagnosis history may be referenced. Specifically, for example, if the number of diagnoses by the diagnostic reading server 250 is more than or equal to the number of diagnoses by the diagnosis server 200 for plurality of pieces or all pieces of the most recent diagnosis history, the AI/diagnostic reading flag indicating the diagnosis server 200 may be set. If the number of diagnoses by the diagnostic reading server 250 is less than the number of diagnoses by the diagnosis server 200, the AI/diagnostic reading flag indicating the diagnostic reading server 250 is may be set.

In Step S1103, if no past diagnosis history for the patient exist, for example, the AI/diagnostic reading flag indicating the diagnosis server 200 may be set or the AI/diagnostic reading flag indicating the diagnostic reading server 250 may be set.

With the processing in FIG. 10, the patient can receive a fair image diagnosis by the diagnosis server 200 and the diagnostic reading server 250 without favoring a particular server. If the physician using the terminal 400 or the prefers a particular server, an AI/diagnostic reading flag indicating the same sever as the image diagnosis source in the most recent diagnosis history may be set. Further, for example, for an initial diagnosis of a patient, an AI/diagnostic reading flag indicating both the diagnosis server 200 and the diagnostic reading server 250 may be set.

In Step S803, the AI/diagnostic reading information setting unit 402 may set the AI/diagnostic reading flag based on the department of the physician using the terminal 400. Specifically, for example, the AI/diagnostic reading information setting unit 402 receives input of the department and sets an AI/diagnostic reading flag indicating the diagnosis server 200 if the department is ophthalmology and sets an AI/diagnostic reading flag indicating the diagnostic reading server 250 if the department is not ophthalmology (e.g., internal medicine).

With this configuration, a physician with knowledge in a ophthalmology department can achieve a sufficient diagnosis result with image diagnosis by the diagnosis server 20 that performs a quick diagnosis using the AI 220 and a physician in a department other than ophthalmology can produce a diagnosis result with findings by a radiologist. If the image diagnosis using the AI 220 is expected to produce more detailed findings than image diagnosis by a radiologist, the AI/diagnostic reading flag indicating the diagnosis server 200 may be set when the department is not ophthalmology and the AI/diagnostic reading flag indicating the diagnostic reading server 250 may be set when the department is ophthalmology.

The AI/diagnostic reading information setting unit 402 may set the AI/diagnostic reading flag based on information related to the installation location of the imaging device 500 in Step S803. Specifically, the terminal 400 holds information indicating correlation between the identification information and the installation location of the imaging device 500. The AI/diagnostic reading information setting unit 402 acquires the identification information of the imaging device 500 that captured the subject eye image and identifies the installation location of the imaging device 500. If the installation location is a facility with an ophthalmologist such as a diabetes center or a hospital with an ophthalmology department, the AI/diagnostic reading information setting unit 402 sets the AI/diagnostic reading flag indicating the diagnosis server 200. If the installation location is a facility without an ophthalmologist such as an internal medicine clinic, the AI/diagnostic reading information setting unit 402 sets the AI/diagnostic reading flag indicating the diagnostic reading server 250.

With this configuration, in a facility with a knowledgeable ophthalmologist such as a diabetes center or a hospital with an ophthalmology department, a sufficient diagnosis result can be obtained with image diagnosis by the diagnosis server 20 that performs a quick diagnosis using the AI 220. Further, a physician other than an ophthalmologist, such as a physician of internal medicine, can obtain a diagnosis result including findings by a radiologist.

If the image diagnosis using the AI 220 is expected to produce more detailed findings than image diagnosis by a radiologist, the AI/diagnostic reading flag indicating the diagnosis server 200 may be set when the installation location is a facility not having an ophthalmologist such as an internal medicine clinic, and the AI/diagnostic reading flag indicating the diagnostic reading server 250 may be set when the installation location is a facility with an ophthalmologist such as a diabetes clinic or a hospital with an ophthalmology department. Using the same method as described above, the AI/diagnostic reading flag may be set based on the installation location of the terminal 400 or the intra-hospital server 300.

Further, in Step S803, the AI/diagnostic reading information setting unit 402 may set the AI/diagnostic reading flag based on pricing information of diagnosis courses compiled from one or more diagnoses including image diagnosis of the fundus image data. Specifically, for example, the AI/diagnostic reading information setting unit 402 receives input of pricing information for diagnosis courses and, if the price is less than a predetermined threshold, sets the AI/diagnostic reading flag indicating the diagnosis server 200 and, if the price is more than or equal to the predetermined threshold, sets the AI/diagnostic reading flag indicating the diagnostic reading server 250.

The diagnosis server 200 automatically performs a diagnosis using the AI 220. However, the diagnostic reading server 250 requires wages for a radiologist and thus diagnosis is expensive. Therefore, by setting the AI/diagnostic reading flag based on the pricing information for diagnosis courses as described above, an appropriate diagnosis can be made based on price. For example, if the diagnosis is more expensive than image diagnosis by the AI 220, the AI/diagnostic reading flag indicating the diagnosis server 200 is set if the price is more than or equal to a predetermined threshold and the AI/diagnostic reading flag indicating the diagnostic reading server 250 is set if the price is less than the predetermined threshold.

In Step S803, the AI/diagnostic reading information setting unit 402 may, for example, set the AI/diagnostic reading flag based on schedule information of the radiologist performing the image diagnosis using the diagnostic reading server 250.

Specifically, the AI/diagnostic reading information setting unit 402 regularly acquires schedule information of the radiologist performing the image diagnosis using the diagnostic reading server 250 (e.g., information indicating when the radiologist can perform an image diagnosis, such as free time of the radiologist). For example, the AI/diagnostic reading information setting unit 402 references the schedule information and sets the AI/diagnostic reading flag indicating the diagnosis server 200 if the time until the radiologist can start image diagnosis is more than or equal to a particular value and sets the AI/diagnostic reading flag indicating the diagnostic reading server 250 when that time is less than the predetermined value.

With this configuration, if the radiologist has a full schedule, image diagnosis can be performed quickly with the AI 220 of the diagnosis server 200 and, when the radiologist is free, image diagnosis based on the radiologist's knowledge can be performed.

In Step S803, the AI/diagnostic reading information setting unit 402 may set the AI/diagnostic reading flag based on, for example, symptom/diagnosis classifications for diagnosis requested by the physician using the terminal 400.

Specifically, the AI/diagnostic reading information setting unit 402 receives input of symptom/diagnosis classifications for diagnosis and sets an AI/diagnostic reading flag indicating that an image diagnosis can be performed according to the symptom/ diagnosis classification. The terminal 400 is preset with information indicating symptom/diagnosis classifications for which diagnosis with the diagnosis server 200 and the diagnostic reading server 250 (physician performing image diagnosis using the diagnostic reading server 250) can be performed.

In Step S803, the AI/diagnostic reading information setting unit 402 may set the AI/diagnostic reading flag based on the angle of view of the subject eye image captured by the imaging device 500. Specifically, the AI/diagnostic reading information setting unit 402 acquires the angle of view of the subject eye image captured by the imaging device 500 from the imaging device 500. The AI/diagnostic reading information setting unit 402 may also be preset with correspondence between the ID of the imaging device 500 and the angle of view and acquire the angle of view according to this correspondence.

The AI/diagnostic reading information setting unit 402 sets the AI/diagnostic reading flag indicating the diagnosis server 200 if the acquired angle of view is more than or equal to a predetermined value and sets the AI/diagnostic reading flag indicating the diagnostic reading server 250 if the acquired angle of view is less than the predetermined value. The AI/diagnostic reading information setting unit 402 may set the AI/diagnostic reading flag indicating the diagnosis server 200 if the acquired angle of view is less than the predetermined value and set the AI/diagnostic reading flag indicating the diagnostic reading server 250 if the acquired angle of view is more than or equal to the predetermined value.

With this configuration, image diagnosis can be performed with the AI 220 of the diagnosis server 200 and by using a subject eye image with an angle of view familiar to the radiologist using the diagnostic reading server 250 (e.g., for precise diagnosis.

The above-described example deals with a case where the terminal 400 collects necessary information to set the AI/diagnostic reading flag, but the intra-hospital server 300 or the administration server 100 may collect necessary information and set the AI/diagnostic reading flag.

For example, even if the AI/diagnostic reading flag is set from the input screen 1000 in FIG. 10, the AI/diagnostic reading information setting unit 402 may select the AI/diagnostic reading flag based on the above-described information. If the AI/diagnostic reading flag selected from the input screen 1000 and the AI/diagnostic reading flag selected by the AI/diagnostic reading information setting unit 402 are different, the AI/diagnostic reading information setting unit 402 may, for example, display the AI/diagnostic reading flag selected by the AI/diagnostic reading information setting unit 402 on a display via the display screen generation unit 403 to recommend that flag to a user, or may set the AI/diagnostic reading flag selected by the AI/diagnostic reading information setting unit 402.

The above-described example deals with a case where the AI/diagnostic reading flag is determined from one type of information, but the AI/diagnostic reading flag may be determined from a plurality of types of information. Specifically, for example, the server selection information 110 is written with conditional branches based on values indicated by the plurality of types of information and the AI/diagnostic reading flag is determined based on the values of the plurality of types of information.

Figure 12:
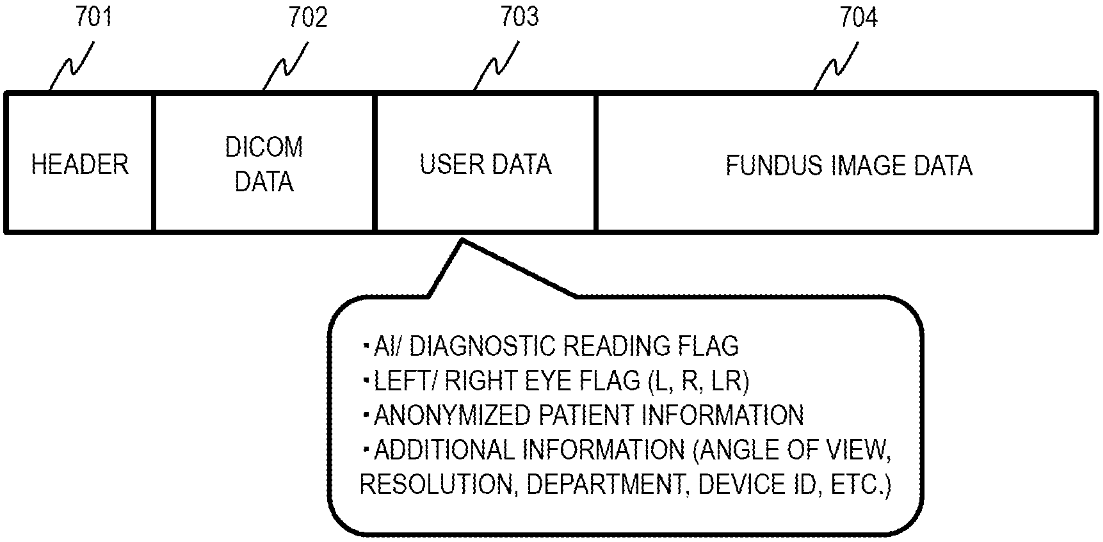
FIG. 12 illustrates an example of a data structure of anonymized data for diagnosis according to the first embodiment.

FIG. 12 illustrates an example of a data structure of the anonymized data for diagnosis sent from the administration server 100 to the diagnosis server 200. The anonymized data for diagnosis includes, for example, a header 701, digital imaging and communications in medicine (DICOM) data 702, user data 703, and fundus image data 704.

The header 701 includes information such as information describing a data format and information on origin and destination of the data. The DICOM data 702 includes, for example, the format of the medical image captured by the imaging device 500 and information defining communication protocols between medical devices including the imaging device 500.

The user data 703 includes, for example, an AI/diagnostic reading flag, a left/right eye flag, the anonymized patient information, and additional information. The left/right eye flag is a flag indicating whether the fundus image data 704 is image data for the right eye, image data for the left eye, or image data for both eyes (e.g., one value among L, R and LR).

The additional information includes, for example, attribute information related to the captured image, such as device information of the imaging device 500, information related to the hospital or physician using the terminal 400, and names of diseases to be diagnosed. Information such as the angle of view, modality and resolution of the image (subject eye image) captured by the imaging device 500 and a device ID of the imaging device 500 are examples of the device information.

"Modality" is information indicating the type of the imaging device 500 (e.g., fundus camera, scanning laser ophthalmoscope, optical coherence tomography machine, etc.) or the type of image (e.g., fundus image or angiogram captured by red laser or near-infrared laser) used as a medical image captured by the imaging device 500. The name of the physician or hospital using the terminal 400 and the installation location of the terminal (information related to department, e.g., ophthalmology, internal medicine or diabetic tract medicine, or information related to facility, e.g., optical retailer or diagnostic facility) is an example of the facility information.

Among the additional information, information that can also be written in the DICOM data 702 such as the terminal ID of the imaging device 500 and the modality may only be written in the DICOM data 702.

Figure 13:
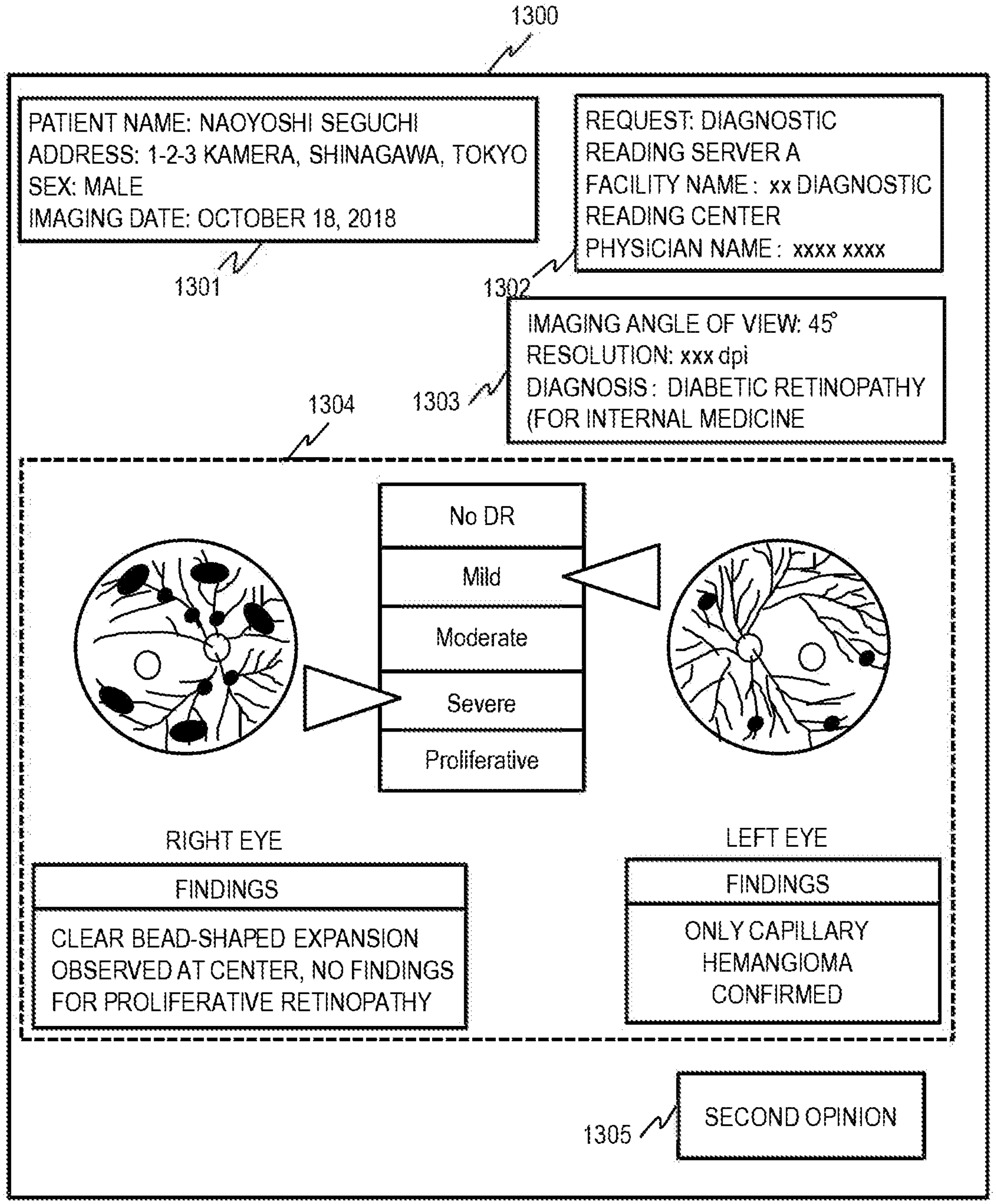
FIG. 13 illustrates an example of display screen that displays a diagnosis result according to the first embodiment.

FIG. 13 illustrates a display screen (screen layout) that displays a diagnosis result. A display screen 1300 includes a patient information display area 1301, a request destination information display area 1302, an additional information display area 1303, a diagnosis result display area 1304, and a second opinion button 1305.

In the patient information display area 1301, patient information included in the image diagnosis data is displayed. In the request destination information display area 1302, information related to a request destination for the image diagnosis is displayed. If the image diagnosis is performed by artificial intelligence of the diagnosis server 200, the ID of the AI 220 or the name of the server that performed the image diagnosis is displayed in the request destination information display area 1302.

If the fundus image data is sent to the diagnostic reading server 250 and a radiologist image diagnosis is performed, the ID of the diagnostic reading server or the name of the server, the name of the diagnostic reading facility including the diagnostic reading server, and the name of the facility and physician that performed the image diagnosis are displayed in the request destination information display area 1302.

In the additional information display area 1303, some or all of the additional information (angle of view, resolution, diagnosis type, etc.) included in the data for diagnosis is displayed. Further, information indicating the diagnosis result of the fundus image data is displayed in the diagnosis result display area 1304. In the example of FIG. 13, fundus images for both eyes, a bar indicating the symptom level among five levels for diabetic retinopathy in both eyes, and findings in both eyes are displayed in the diagnosis result display area 1304.

In the example of FIG. 13, a right arrow (indicator) indicating the symptom level of diabetic retinopathy in the fundus image of the right eye and the right eye is displayed to the right of the bar, and a right arrow indicating the symptom level of diabetic retinopathy in the fundus image of the left eye and the left eye is displayed to the left of the bar. With this configuration, the user is able to understand the symptom level for diabetic retinopathy in both eyes and the differences between symptom levels by simply looking at the diagnosis result display area 1304.

The second opinion button 1305 is a button used to request a second opinion from another server. If the image diagnosis is performed by the diagnosis server 200 and the second opinion button 1305 is selected, a notification is issued to the administration server 100 so as to send anonymized image diagnosis data to the diagnostic reading server 250.

If the fundus image data is sent to the diagnostic reading server 250 and the image diagnosis is performed by a radiologist and the second opinion button 1305 is selected, a notification is issued to the administration server 100 so as to send anonymized image diagnosis data to the diagnosis server 200. With this configuration, the image diagnosis can be performed by another server as a second opinion after the physician and patient have seen the image diagnosis result.

Further, the second opinion button 1305 may only be displayed when the symptom in the image diagnosis result is worse than a predetermined level (e.g., Mild or worse in FIG. 13). If the symptom in the image diagnosis result is worse than the predetermined level, image diagnosis by another server may be performed automatically without the second opinion button 1305 being displayed.

Further, the second opinion button 1305 may be displayed if image diagnosis is performed by the AI 220 of the diagnosis server 200 that can determine the onset of a disease but not the symptom level of the disease. The administration server 100 may further hold information related to correspondence between diseases and a sever that can diagnose symptom levels of the diseases.

If the second opinion button 1305 is selected in this case, the administration server 100 references the correspondence information to identify a server that can diagnose symptom levels of diseases. The administration server 100 may send information indicating the identified server to the intra-hospital server 300 and display the information, or may send re-anonymized data for diagnosis to the identified server and request image diagnosis.

Further, the diagnosis server 200 and/or diagnostic reading server 250 that performed the image diagnosis may include a second opinion instruction in the encrypted image diagnosis result and send this diagnosis result. Specifically, a second opinion instruction is generated if the AI 220 of the diagnosis server 200 determines that a second opinion is necessary (e.g., if it is determined that a disease is present) or the diagnostic reading server 250 receives input of the second opinion instruction from a user (e.g., radiologist).

The second opinion button 1305 may only be displayed when a second opinion instruction is included in the encrypted image diagnosis result, or image diagnosis by another server may be automatically performed without the second opinion button 1305 being displayed when a second opinion instruction is included in the encrypted image diagnosis result.

Figure 14:
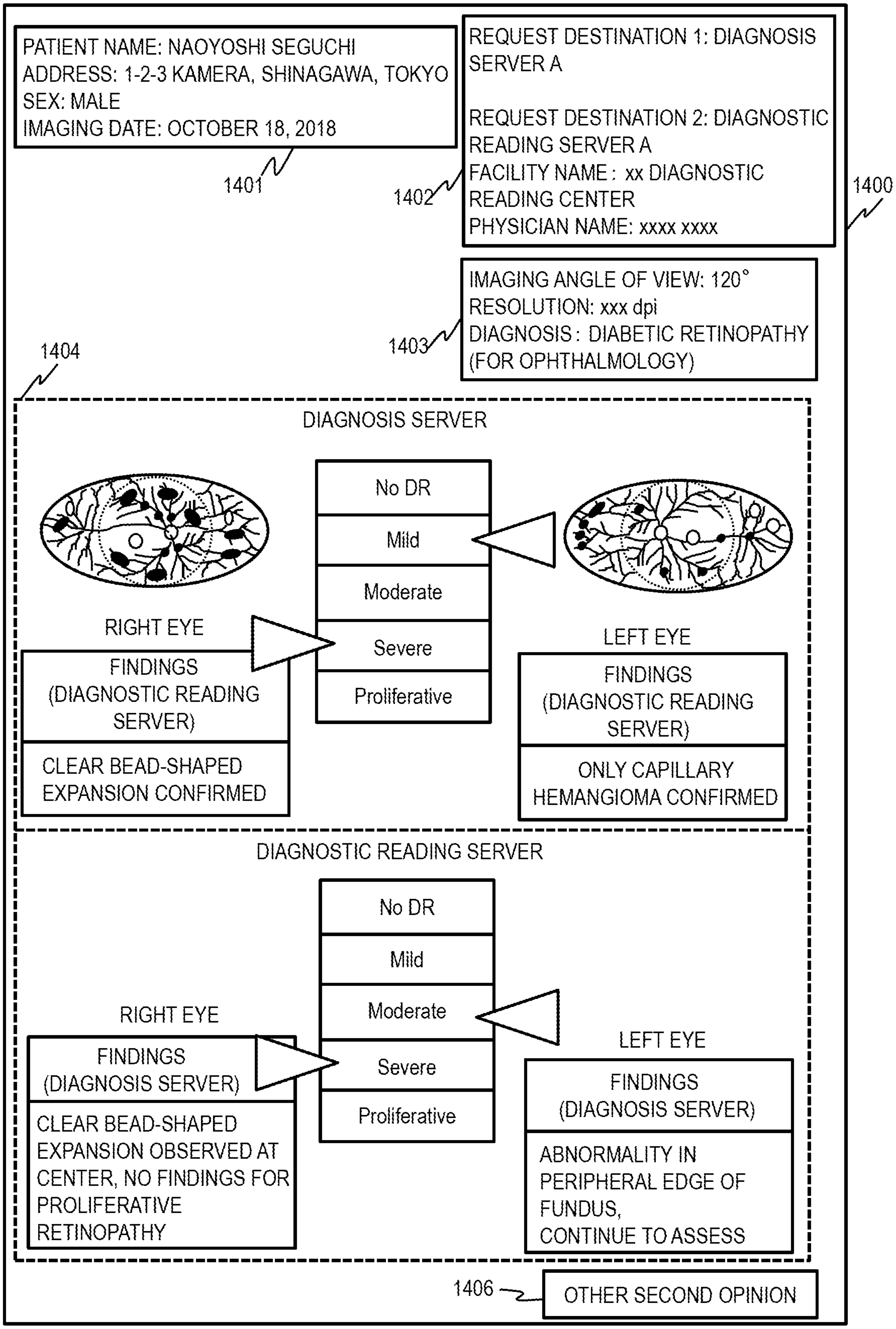
FIG. 14 illustrates an example of display screen that displays a diagnosis result according to the first embodiment.

FIG. 14 illustrated an example of a display screen that displays a diagnosis result when a second opinion is received. In FIG. 14, Request Destination 1 that performed the initial diagnosis is artificial intelligence and Request Destination 2 that performed a diagnosis as a second opinion is a radiologist. A display screen 1400 includes a patient information display area 1401, a request destination information display area 1402, an additional information display area 1403, a diagnosis result display area 1404, and another second opinion button 1406. The content displayed in the patient information display area 1401 and the additional information display area 1403 is the same as the content displayed in the patient information display area 1301 and the display area 1303 in FIG. 13, respectively.

Differences to FIG. 13 will be described. Information related to the Request Destination 1 and the Request Destination 2 is displayed in the request destination information display area 1402. In FIG. 14, "Diagnosis Server A" is displayed as the Request Destination 1 and "Diagnostic Reading Server A", which is the name of the diagnostic reading server, "XX Diagnostic Reading Center", which is the name of the diagnostic reading facility including the diagnostic reading server, and the names of the facility and physician who performed the image diagnosis are displayed as the Request Destination 2.

The subject eye images for both eyes, a bar indicating the symptom level of diabetic retinopathy in both eyes, and findings in both eyes for both an initial diagnosis and a second opinion diagnosis are displayed in the diagnosis result display area 1404. Operating the other second opinion button 1406 makes it possible to receive a diagnosis as a second opinion from another Request Destination 3 different from the Request Destination 1 and the Request Destination 2.

As illustrated in the display screen 1400 in FIG. 14, displaying both diagnosis results allows the user of the intra-hospital server 300 and the terminal 400 to obtain a more accurate diagnosis result as a combination of the two results.

The present invention is not limited to the above-described embodiments and these embodiments may be combined as desired. Further, other embodiments are included in the scope of the present invention without departing from the technical scope of the present invention.

EXPLANATION OF REFERENCES

100 administration server, 101 anonymization processing unit, 102 server selection unit, 103 display screen generation unit, 104 diagnosis result data generation unit, 200 diagnosis server, 201 image diagnosis unit, 202 training information management unit, 203 diagnosis image generation unit, 204 management unit, 210 training DB, 211 image diagnosis model, 250 diagnostic reading server, 251 diagnosis screen generation unit, 252 diagnosis information management unit, 253 management unit, 260 diagnosis information DB, 300 intra-hospital server, 301 anonymization processing unit, 302 patient information management unit, 303 display screen generation unit, 310 patient information DB, 400 terminal, 401 data for diagnosis generation unit, 402 AI/diagnostic reading information setting unit, 403 display screen generation unit, 600 calculator, 601 processor, 602 storage device, 603 input device, 604 output device, 605 communication IF

What is claimed is:

1. An information processing system comprising:

an image device which acquires subject eye image data of a patient;

a first information processing device which stores the subject eye image data that is communicated with the image device;

a second information processing device which performs image diagnosis on the subject eye image data that is communicated with the first information device, using artificial intelligence;

a third information processing device which acquires diagnosis results of image diagnosis performed on the subject eye image data by a radiologist, the subject eye image data being communicated with the first information processing device; and a terminal which is a processing device associated with a physician, wherein:

the terminal is configured to:

acquire patient data relating to information of the patient from the physician;

acquire the subject eye image data of the patient from the image device;

receive, from a user interface, a selection of diagnosis method from among artificial intelligence, a radiologist, or a combination of artificial intelligence and a radiologist;

generate a flag indicating either diagnosis using artificial intelligence or diagnosis by a radiologist, the flag being generated based on at least in part from a group of an image diagnosis result for the subject eye image data, a past diagnosis history, a number of diagnoses, a department of a physician using the terminal, an installation location of the department, pricing information of a diagnosis course, a schedule of the radiologist, a symptom to be diagnosed, a diagnosis classification, and an angle of view of the subject eye image data;

set the flag to indicate either diagnosis using artificial intelligence or diagnosis by the radiologist; and transmit the subject eye image data and the flag to the first information processing device to selectively control, based on the flag; and the first information processing device is configured to:

anonymize the patient data using a predetermined algorithm;

select, based on the flag, a device from among the second information processing device or the third information processing device such that the second information processing device is selected to perform a faster and less expensive diagnosis and the third information processing device is selected to perform a more precise diagnosis;

transmit, to the selected device, the anonymized patient data, the subject eye image data, and the flag;

receive, from the selected device, an encrypted diagnosis result;

use a decryption key to generate a decrypted diagnosis result and obtain, based on the anonymized patient data, the patient information associated with the decrypted diagnosis result; and display, on a display screen, the decrypted diagnosis result and the patient information.

2. The information processing system according to claim 1, wherein the first information processing device transmits, based on the flag, the subject eye image data to the second information processing device or the third information processing device.

3. The information processing system according to claim 2, wherein the second information processing device transmits a diagnosis result of the image diagnosis using artificial intelligence to the first information processing device when having received the subject eye image data from the first information processing device, and wherein the third information processing device transmits diagnosis results of the image diagnosis by the radiologist to the first information processing device when having received the subject eye image data from the first information processing device.

4. The information processing system according to claim 3, wherein, when the flag indicates image diagnosis by the radiologist and the first information processing device receives a diagnosis recommendation instruction recommending image diagnosis using artificial intelligence from a third processing device, the first information processing device transmits the subject eye image data to the second information processing device.

5. The information processing system according to claim 3, wherein, when the flag indicates image diagnosis by the radiologist and the first information processing device receives a diagnosis recommendation instruction recommending image diagnosis by the radiologist from the second processing device, the first information processing device transmits the subject eye image data to the third information processing device.

6. The information processing system according to claim 3, wherein, when the flag indicates image diagnosis by the radiologist and the first information processing device receives a diagnosis recommendation instruction recommending image diagnosis using artificial intelligence from the third information processing device, the first information processing device transmits the diagnosis recommendation instruction to the terminal, and the terminal displays the diagnosis recommendation instruction.

7. The information processing system according to claim 3, wherein, when the flag indicates image diagnosis using artificial intelligence and the first information processing device receives a diagnosis recommendation instruction recommending image diagnosis by the radiologist from the second information processing device, the first information processing device transmits the diagnosis recommendation instruction to the terminal, and the terminal displays the diagnosis recommendation instruction.

8. The information processing system according to claim 3, wherein, when the flag indicates diagnosis using artificial intelligence and a diagnosis result received by the first information processing device from the second information processing device satisfies a predetermined condition, the first information processing device transmits the subject eye image data to the third information processing device.

9. The information processing system according to claim 3, wherein, when the flag indicates diagnosis by the radiologist and a diagnosis result received by the first information processing device from the third information processing device satisfies a predetermined condition, the first information processing device transmits the subject eye image data to the second information processing device.

10. The information processing system according to claim 3, wherein, when the flag indicates diagnosis using artificial intelligence and a diagnosis result received by the first information processing device from the second information processing device satisfies a predetermined condition, the first information processing device transmits a diagnosis recommendation instruction recommending image diagnosis by the radiologist to the terminal, and the terminal displays the diagnosis recommendation instruction.

11. The information processing system according to claim 3, wherein, when the flag indicates diagnosis by the radiologist and a diagnosis result received by the first information processing device from the second information processing device satisfies a predetermined condition, the first information processing device transmits a diagnosis recommendation instruction recommending image diagnosis using artificial intelligence to the terminal, and the terminal displays the diagnosis recommendation instruction.

12. The information processing system according to claim 8, wherein the predetermined condition is the diagnosis result indicating that a lesion is present in the subject eye of a patient in the subject eye image data.

13. The information processing system according to claim 2, wherein, when the flag indicates image diagnosis by the radiologist, the first information processing device transmits the subject eye image data to the second information processing device and the third information processing device;

the second information processing device stores the subject eye image data; and the third information processing device transmits a diagnosis result of the image diagnosis of the received subject eye image data to the first information processing device.

14. The information processing system according to claim 1, wherein the subject eye image data includes at least one of fundus image data obtained by a fundus camera, fundus image data obtained by a scanning laser ophthalmoscope, and tomographic data obtained by optical coherence tomography.

* * * * *